(12) United States Patent
Dasari et al.

(10) Patent No.: US 11,559,795 B2
(45) Date of Patent: Jan. 24, 2023

(54) BIMETALLIC CATALYSTS SUPPORTED ON ZEOLITES FOR SELECTIVE CONVERSION OF N-BUTANE TO ETHANE

(71) Applicant: Sabic Global Technologies, B.V., Bergen Op Zoom (NL)

(72) Inventors: Prasanna Dasari, Sugar Land, TX (US); MyatNoeZin Myint, Sugar Land, TX (US); Katherine Barton, Sugar Land, TX (US); Neeta Kulkarni, Sugar Land, TX (US); Ashim Ghosh, Sugar Land, TX (US); Raul Velasco Pelaez, Sugar Land, TX (US); Dustin Fickel, Sugar Land, TX (US); Heng Shou, Sugar Land, TX (US)

(73) Assignee: Sabic Global Technologies, B.V., Bergen op Zoom (NL)

( * ) Notice: Subject to any disclaimer, the term of this patent is extended or adjusted under 35 U.S.C. 154(b) by 0 days.

(21) Appl. No.: 17/262,288

(22) PCT Filed: Sep. 17, 2019

(86) PCT No.: PCT/US2019/051470
§ 371 (c)(1),
(2) Date: Jan. 22, 2021

(87) PCT Pub. No.: WO2020/061012
PCT Pub. Date: Mar. 26, 2020

(65) Prior Publication Data
US 2021/0316285 A1    Oct. 14, 2021

Related U.S. Application Data

(60) Provisional application No. 62/733,309, filed on Sep. 19, 2018.

(51) Int. Cl.
*B01J 29/06* (2006.01)
*B01J 29/44* (2006.01)
(Continued)

(52) U.S. Cl.
CPC .............. *B01J 29/44* (2013.01); *B01J 6/001* (2013.01); *B01J 29/035* (2013.01); *B01J 29/0352* (2013.01); *B01J 29/0354* (2013.01); *B01J 29/0356* (2013.01); *B01J 29/0358* (2013.01); *B01J 29/043* (2013.01); *B01J 29/044* (2013.01); *B01J 29/045* (2013.01); *B01J 29/061* (2013.01); *B01J 29/064* (2013.01); *B01J 29/068* (2013.01); *B01J 29/072* (2013.01); *B01J 29/076* (2013.01);
(Continued)

(58) Field of Classification Search
CPC ...... B01J 29/061; B01J 29/064; B01J 29/068; B01J 29/072; B01J 29/076; B01J 29/084; B01J 29/106; B01J 29/126; B01J 29/146; B01J 29/166; B01J 29/035; B01J 29/0352; B01J 29/0354; B01J 29/0356; B01J 29/0358; B01J 29/043; B01J 29/045; B01J 29/044; B01J 29/44; B01J 29/42; B01J 29/46; B01J 29/48; B01J 29/68; B01J 29/69; B01J 29/67; B01J 29/66; B01J 29/64; B01J 29/63; B01J 29/62; B01J 29/61; B01J 29/723; B01J 29/743; B01J 29/763; B01J 29/783; B01J 29/7057; B01J 29/7215; B01J 29/7415; B01J 29/7615; B01J 29/7246; B01J 29/7446; B01J 29/7646; B01J 29/7846; B01J 2229/186; B01J 2229/20; B01J 2229/42; B01J 37/0209; B01J 37/0236; B01J 37/16; B01J 37/0009; B01J 6/001; C07C 2529/44; C07C 2529/46; C07C 2529/48; C07C 2529/06; C07C 2529/068; C07C 2529/072; C07C 2529/076; C07C 2529/62; C07C 2529/63; C07C 2529/64; C07C 2529/67; C07C 2529/68; C07C 2529/69; C07C 2529/74; C07C 2529/76; C07C 2529/78; C07C 4/10; C07C 9/12; C07C 9/06; C07C 9/04; C07C 9/08; C07C 6/08; C07C 6/10
USPC ........ 502/60, 63, 64, 66, 69, 71, 74, 77, 79; 585/734, 739, 752
See application file for complete search history.

(56) References Cited

U.S. PATENT DOCUMENTS

| | | | |
|---|---|---|---|
| 4,137,147 A | 1/1979 | Franck et al. | |
| 4,140,621 A | 2/1979 | Franck et al. | |

(Continued)

FOREIGN PATENT DOCUMENTS

| | | | |
|---|---|---|---|
| CN | 107109257 A | 8/2017 | |
| CN | 107223119 A | 9/2017 | |

(Continued)

OTHER PUBLICATIONS

Notice of Allowance and Fee(s) Due, U.S. Appl. No. 17/262,286, dated Nov. 9, 2021, 14 pages.
(Continued)

*Primary Examiner* — Elizabeth D Wood
(74) *Attorney, Agent, or Firm* — Rodney B. Carroll; Conley Rose, P.C.

(57) ABSTRACT

A hydrogenolysis bimetallic supported catalyst comprising a first metal, a second metal, and a zeolitic support; wherein the first metal and the second metal are different; and wherein the first metal and the second metal can each independently be selected from the group consisting of iridium (Ir), platinum (Pt), rhodium (Rh), ruthenium (Ru), palladium (Pd), molybdenum (Mo), tungsten (W), nickel (Ni), and cobalt (Co).

20 Claims, No Drawings

(51) Int. Cl.

| | |
|---|---|
| *B01J 6/00* | (2006.01) |
| *B01J 37/02* | (2006.01) |
| *B01J 37/16* | (2006.01) |
| *C07C 4/10* | (2006.01) |
| *B01J 29/14* | (2006.01) |
| *B01J 29/12* | (2006.01) |
| *B01J 29/068* | (2006.01) |
| *B01J 29/072* | (2006.01) |
| *B01J 29/035* | (2006.01) |
| *B01J 29/04* | (2006.01) |
| *B01J 29/076* | (2006.01) |
| *B01J 29/064* | (2006.01) |
| *B01J 29/08* | (2006.01) |
| *B01J 29/16* | (2006.01) |
| *B01J 29/10* | (2006.01) |
| *B01J 29/64* | (2006.01) |
| *B01J 29/42* | (2006.01) |
| *B01J 29/67* | (2006.01) |
| *B01J 29/69* | (2006.01) |
| *B01J 29/68* | (2006.01) |
| *B01J 29/70* | (2006.01) |
| *B01J 29/61* | (2006.01) |
| *B01J 29/74* | (2006.01) |
| *B01J 29/46* | (2006.01) |
| *B01J 29/76* | (2006.01) |
| *B01J 29/78* | (2006.01) |
| *B01J 29/48* | (2006.01) |
| *B01J 29/62* | (2006.01) |
| *B01J 29/72* | (2006.01) |
| *B01J 29/66* | (2006.01) |
| *B01J 29/63* | (2006.01) |
| *B01J 37/00* | (2006.01) |
| *C07C 9/04* | (2006.01) |
| *C07C 9/06* | (2006.01) |
| *C07C 6/10* | (2006.01) |
| *C07C 6/08* | (2006.01) |
| *C07C 9/08* | (2006.01) |
| *C07C 9/12* | (2006.01) |

(52) U.S. Cl.
CPC .......... *B01J 29/084* (2013.01); *B01J 29/106* (2013.01); *B01J 29/126* (2013.01); *B01J 29/146* (2013.01); *B01J 29/166* (2013.01); *B01J 29/42* (2013.01); *B01J 29/46* (2013.01); *B01J 29/48* (2013.01); *B01J 29/61* (2013.01); *B01J 29/62* (2013.01); *B01J 29/63* (2013.01); *B01J 29/64* (2013.01); *B01J 29/66* (2013.01); *B01J 29/67* (2013.01); *B01J 29/68* (2013.01); *B01J 29/69* (2013.01); *B01J 29/7057* (2013.01); *B01J 29/723* (2013.01); *B01J 29/7215* (2013.01); *B01J 29/7246* (2013.01); *B01J 29/743* (2013.01); *B01J 29/7415* (2013.01); *B01J 29/7446* (2013.01); *B01J 29/763* (2013.01); *B01J 29/7615* (2013.01); *B01J 29/7646* (2013.01); *B01J 29/783* (2013.01); *B01J 29/7846* (2013.01); *B01J 37/0009* (2013.01); *B01J 37/0209* (2013.01); *B01J 37/0236* (2013.01); *B01J 37/16* (2013.01); *C07C 4/10* (2013.01); *C07C 6/08* (2013.01); *C07C 6/10* (2013.01); *C07C 9/04* (2013.01); *C07C 9/06* (2013.01); *C07C 9/08* (2013.01); *C07C 9/12* (2013.01); *B01J 2229/186* (2013.01); *B01J 2229/20* (2013.01); *B01J 2229/42* (2013.01); *C07C 2529/06* (2013.01); *C07C 2529/072* (2013.01); *C07C 2529/076* (2013.01); *C07C 2529/08* (2013.01); *C07C 2529/44* (2013.01); *C07C 2529/46* (2013.01); *C07C 2529/48* (2013.01); *C07C 2529/62* (2013.01); *C07C 2529/63* (2013.01); *C07C 2529/64* (2013.01); *C07C 2529/67* (2013.01); *C07C 2529/68* (2013.01); *C07C 2529/69* (2013.01); *C07C 2529/74* (2013.01); *C07C 2529/76* (2013.01); *C07C 2529/78* (2013.01)

(56) References Cited

U.S. PATENT DOCUMENTS

| | | | |
|---|---|---|---|
| 4,166,077 A | | 8/1979 | Bernard et al. |
| 4,329,516 A | | 5/1982 | Al-Muddarris |
| 4,472,535 A | * | 9/1984 | Chang .................... B01J 29/076 |
| | | | 518/715 |
| 4,680,355 A | | 7/1987 | Nakahara |
| 4,731,490 A | | 3/1988 | Coughenour et al. |
| 4,754,078 A | | 6/1988 | Vora et al. |
| 5,313,004 A | | 5/1994 | Harandi et al. |
| 6,897,345 B2 | | 5/2005 | Marchionna et al. |
| 9,011,672 B2 | | 4/2015 | Etter et al. |
| 9,850,438 B2 | | 12/2017 | Oprins |
| 9,981,254 B2 | * | 5/2018 | Jana ...................... B01J 29/068 |
| 2002/0026087 A1 | | 2/2002 | Nierlich et al. |
| 2008/0029434 A1 | | 2/2008 | Brewer et al. |
| 2008/0128324 A1 | | 6/2008 | Hansen et al. |
| 2011/0040133 A1 | | 2/2011 | Vermeiren et al. |
| 2011/0257451 A1 | * | 10/2011 | Thorman ................ C07C 2/867 |
| | | | 585/435 |
| 2013/0066126 A1 | * | 3/2013 | Jana ........................ B01J 29/46 |
| | | | 502/64 |
| 2015/0231614 A1 | * | 8/2015 | Jana ...................... B01J 29/7007 |
| | | | 585/510 |
| 2016/0137933 A1 | | 5/2016 | Ward et al. |
| 2016/0176778 A1 | * | 6/2016 | Jan ............................ C07C 2/76 |
| | | | 585/417 |
| 2016/0362617 A1 | | 12/2016 | Oprins et al. |
| 2017/0369795 A1 | | 12/2017 | Oprins et al. |
| 2018/0117566 A1 | | 5/2018 | Witte et al. |

FOREIGN PATENT DOCUMENTS

| | | |
|---|---|---|
| WO | 2012071137 A1 | 5/2012 |
| WO | 2017072698 A1 | 5/2017 |
| WO | 2017089938 A1 | 6/2017 |
| WO | 2020061010 A1 | 3/2020 |
| WO | 2020061011 A1 | 3/2020 |
| WO | 2020061012 A1 | 3/2020 |

OTHER PUBLICATIONS

Foreign Communication from Related Application—Office Action of German Patent Application No. 11 2019 004 683.7 dated Jun. 3, 2022 2 pages.
Foreign Communication from Related Application—Chinese Office Action with English Translation, CN Patent Application No. 201980061097.8 filed Sep. 17, 2019, 15 pages.
Filing Receipt, Specification and Drawings for U.S. Appl. No. 62/733,284, entitled "Selective Hydrogenolysis Integrated with Cracking," filed Sep. 19, 2018, 41 pages.
Filing Receipt, Specification and Drawings for U.S. Appl. No. 62/733,302, entitled "Selective Hydrogenolysis Integrated with MTBE Production," filed Sep. 19, 2018, 44 pages.
Filing Receipt, Specification and Drawings for U.S. Appl. No. 62/733,309, entitled "Bimetallic Catalysts Supported on Zeolites for Selective Conversion of N-Butane to Ethane," filed Sep. 19, 2018, 44 pages.
Foreign Communication from Related Application—International Search Report and Written Opinion of the International Searching Authority, International Application No. PCT/US2019/051463, dated Jan. 3, 2020, 11 pages.

(56) References Cited

OTHER PUBLICATIONS

Foreign Communication from Related Application—International Search Report and Written Opinion of the International Searching Authority, International Application No. PCT/US2019/051469, dated Jan. 3, 2020, 10 pages.

Foreign Communication from Related Application—International Search Report and Written Opinion of the International Searching Authority, International Application No. PCT/US2019/051470, dated Jan. 3, 2020, 10 pages.

Bernard, J.R., et al., "A Selective Route for the Hydrogenolysis of Alkanes into Ethane," Studies in Surface Science and Catalysis, 1981, pp. 149-159, vol. 7.

Bond, Geoffrey C., et al., "Hydrogenolysis of Propane, n-Butane, and Isobutane over Variously Pretreated Ru/TiO2 Catalysts," Journal of Physical Chemistry, 1986, pp. 4877-4881, vol. 90, No. 20, American Chemical Society.

Jackson, S.D. et al., "Supported Metal Catalysts; Preparation, Characterisation, and Function; Part IV. Hydrogenolysis of Ethane, Propane, n-Butance and iso-Butane over Supported Platinum Catalysts" Journal of Catalysis, 1998, pp. 225-234, vol. 176, Academic Press.

Kozlov, I.T. et al., "Selective Hydrocracking of Light Naphtha Cuts," Chemistry and Technology of Fuels and Oils, Jul. 1985, pp. 346-349, vol. 21, No. 7, Plenum Publishing Corporation.

Sinfelt, J.H.,"Catalytic Hydrogenolysis on Metals," Catalysis Letters, 1991, pp. 159-172, vol. 9, J.C. Baltzer A.G. Scientific Publishing Company.

Communication from a related application—Office Action U.S. Appl. No. 17/262,287, dated Jul. 15, 2022, 14 pages.

Foreign Communication from Related Application—Second Chinese Office Action with English Translation, dated Jun. 20, 2022, CN Patent Application No. 201980061097.8 filed Sep. 17, 2019, 7 pages.

Foreign Communication from Related Application—Saudi Arabian Office Action with English Translation, dated Oct. 11, 2022, SA Patent Application No. 521421466 filed Mar. 15, 2021, 12 pages.

Notice of Allowance and Fees dated Nov. 15, 2022, U.S. Appl. No. 17/262,287, filed Jan. 22, 2021.

\* cited by examiner

BIMETALLIC CATALYSTS SUPPORTED ON ZEOLITES FOR SELECTIVE CONVERSION OF N-BUTANE TO ETHANE

CROSS-REFERENCE TO RELATED APPLICATION

This application is a filing under 35 U.S.C. 371 of International Application No. PCT/US2019/051470, filed Sep. 17, 2019, entitled "Bimetallic Catalysts Supported on Zeolites for Selective Conversion of n-Butane to Ethane," which claims priority to U.S. Provisional Application No. 62/733,309, filed Sep. 19, 2018, which applications are incorporated by reference herein in their entirety.

TECHNICAL FIELD

The present disclosure relates to methods of processing butanes, more specifically methods of reactive separation of n-butane and i-butane.

BACKGROUND

Butanes are generally produced by natural gas processing and/or oil refining. Butanes can be subjected to cracking in order to produce more valuable chemical intermediates, such as ethylene. Conventional steam cracking of butanes can generate a significant amount of undesired methane, $C_4$ compounds (other than butanes), and heavies, thereby demanding an intensive separation process and lowering the overall carbon efficiency of the process, especially towards desired light olefins such as ethylene. Thus, there is an ongoing need for the development of methods for processing butanes.

DETAILED DESCRIPTION

Disclosed herein are hydrogenolysis bimetallic supported catalysts and methods of making and using same. In an aspect, a hydrogenolysis bimetallic supported catalyst can comprise a first metal and a second metal supported on a zeolite; wherein the first metal and the second metal are different; and wherein the first metal and the second metal can each independently be selected from the group consisting of iridium (Ir), platinum (Pt), rhodium (Rh), ruthenium (Ru), palladium (Pd), molybdenum (Mo), tungsten (W), nickel (Ni), and cobalt (Co). The first metal and the second metal (e.g., Pt and Ir) can be impregnated on a zeolite, such as ZSM-5.

The hydrogenolysis bimetallic supported catalysts disclosed herein can be used to convert a mixed butane stream (e.g., field-grade butane) to desirable products, such as ethane and propane, for example via selective butane hydrogenolysis. In an aspect, n-butane can be selectively converted in the presence of the hydrogenolysis bimetallic supported catalysts disclosed herein to methane, ethane and propane, while i-butane conversion is reduced or eliminated, thereby mitigating methane formation. In such aspect, the recovery of unreacted i-butane from the product stream of hydrogenolysis can provide for a reactive separation of straight-chained hydrocarbons from branched hydrocarbons. The hydrogenolysis gas product stream that remains after recovery of the unreacted i-butane can be further subjected to steam cracking to produce ethylene.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through the carbon of the carbonyl group.

As used herein, the terms "$C_x$ hydrocarbons" and "$C_xs$" are interchangeable and refer to any hydrocarbon having x number of carbon atoms (C). For example, the terms "$C_4$ hydrocarbons" and "$C_4s$" both refer to any hydrocarbons having exactly 4 carbon atoms, such as n-butane, iso-butane, cyclobutane, 1-butene, 2-butene, isobutylene, butadiene, and the like, or combinations thereof.

As used herein, the term "$C_{x+}$ hydrocarbons" refers to any hydrocarbon having equal to or greater than x carbon atoms (C). For example, the term "$C_2+$ hydrocarbons" refers to any hydrocarbons having 2 or more carbon atoms, such as ethane, ethylene, $C_3$s, $C_4$s, $C_5$s, etc.

In an aspect, a hydrogenolysis bimetallic supported catalyst as disclosed herein can comprise a first metal, a second metal, and a zeolitic support; wherein the first metal and the second metal are different. In such aspect, the first metal and the second metal can each independently be selected from the group consisting of iridium (Ir), platinum (Pt), rhodium (Rh), ruthenium (Ru), palladium (Pd), molybdenum (Mo), tungsten (W), nickel (Ni), and cobalt (Co).

In an aspect, the first metal and the second metal can each independently be one or more metals from Group 6 of the Periodic Table; one or more metals from Group 8 of the Periodic Table; one or more metals from Group 9 of the Periodic Table; one or more metals from Group 10 of the Periodic Table; or combinations thereof; wherein the first metal and the second metal are different.

In some aspects, the first metal comprises Pt, and the second metal comprises Ir. In other aspects, the first metal comprises Pt, and the second metal comprises Rh. In yet other aspects, the first metal comprises Pt, and the second metal comprises Ir and Rh.

In an aspect, the first metal and the second metal can be present in the hydrogenolysis bimetallic supported catalyst in a weight ratio of first metal to second metal of from about 0.1:1 to about 10:1, alternatively from about 0.5:1 to about 7:1, alternatively from about 1:1 to about 4:1, alternatively from about 0.3:1 to about 3:1, alternatively from about 0.5:1 to about 2:1, alternatively from about 0.7:1 to about 1.5:1, or alternatively from about 0.8:1 to about 1.2:1.

In an aspect, the first metal and the second metal can be present in the hydrogenolysis bimetallic supported catalyst in a total amount (i.e., first metal amount+second metal amount) of from about 0.1 wt. % to about 10 wt. %, alternatively from about 0.15 wt. % to about 5 wt. %, alternatively from about 0.2 wt. % to about 1 wt. %, alternatively from about 0.4 wt. % to about 0.8 wt. %, or alternatively from about 0.5 wt. % to about 0.7 wt. %, based on the total weight of the hydrogenolysis bimetallic supported catalyst.

In an aspect, a hydrogenolysis bimetallic supported catalyst as disclosed herein can comprise a zeolitic support. For purposes of the disclosure herein the term "zeolitic support(s)" includes zeolitic structures, zeolitic frameworks, aluminosilicates, aluminosilicates structures, aluminosilicates frameworks, zeolite-type materials, zeolite-type structures, zeolite-type frameworks, molecular sieves, silicoaluminophosphates, silicoaluminophosphates structures, silicoaluminophosphates frameworks, aluminophosphates, aluminophosphates structures, aluminophosphates frameworks, and the like, or combinations thereof. Further, for purposes of the disclosure herein, zeolitic structures, zeolitic frameworks, aluminosilicates, aluminosilicates structures, aluminosilicates frameworks, zeolite-type materials, zeolite-type structures, zeolite-type frameworks, molecular sieves, silicoaluminophosphates, silicoaluminophosphates structures, silicoaluminophosphates frameworks, aluminophosphates, aluminophosphates structures, aluminophosphates frameworks, and the like, or combinations thereof are referred to herein collectively as "zeolites."

In some aspects, the zeolitic support can consist of or consist essentially of a zeolite. In other aspects, the zeolitic support can comprise a zeolite and one or more additional compounds such as a binder. Generally a binder can be used to improve mechanical properties of zeolites (e.g., improve resistance to attrition). Nonlimiting examples of binders suitable for use in the hydrogenolysis bimetallic supported catalyst as disclosed herein include alumina, titania, silica, and the like, or combinations thereof. In some aspects, a zeolitic support can comprise from about 70 wt. % to about 90 wt. %, alternatively from about 75 wt. % to about 85 wt. %, or alternatively about 80 wt. % zeolite; and from about 10 wt. % to about 30 wt. %, alternatively from about 15 wt. % to about 25 wt. %, or alternatively about 20 wt. % binder (e.g., alumina binder); based on the total weight of the zeolitic support.

The zeolitic support can comprise zeolites such as small pore zeolites, medium pore zeolites, large pore zeolites, or combinations thereof. Zeolites are inorganic crystalline solids having a framework structure with channels and cavities with characteristic pore geometry. Zeolites can be classified according to their pore openings. For example, small pore zeolites have 8 membered ring pore openings, which can be characterized by a pore size (e.g., diameter of the pore opening) of from 3 Å to 4.5 Å; medium pore zeolites have 10 membered ring pore openings, which can be characterized by a pore size (e.g., diameter of the pore opening) of from 4.5 Å to 6.0 Å; and large pore zeolites have 12 membered ring pore openings, which can be characterized by a pore size (e.g., diameter of the pore opening) of from 6.0 Å to 8.0 Å.

In some aspects, the zeolitic support can comprise one or more aluminosilicate zeolites containing $SiO_4$ and $AlO_4$ tetrahedra in their structure (e.g., framework structure). In other aspects, the zeolitic catalyst can comprise a zeolite-type material, such as silicoaluminophosphates (SAPOs) containing $PO_4$, $AlO_4$ and $SiO_4$ tetrahedra in the structure (e.g., framework structure); and/or aluminophosphates (AlPOs) containing $PO_4$, and $AlO_4$ tetrahedra in the structure (e.g., framework structure). The $SiO_4$, $AlO_4$ and/or $PO_4$ tetrahedra share oxygen atoms, wherein the framework structures have well defined channels and cavities (e.g., pores). These cavities may generally contain exchangeable cations, such as $H^+$, $Na^+$ and $K^+$. Without wishing to be limited by theory, in the zeolite framework structure or zeolite-type framework structure, Si or Al or P can be partially substituted by other tri-valent or tetra-valent elements, such as Ge, Ga, B, etc. Further, and without wishing to be limited by theory, in zeolites, Si or Al or P can also be partially substituted by one or more elements selected from the group consisting of titanium, nickel, copper, magnesium, tin, cobalt, iron, zinc, tungsten, vanadium, gallium, calcium, manganese, ruthenium and rhenium.

Without wishing to be limited by theory, zeolites are generally characterized by a certain acidity, owing to the presence of Brønsted acid sites and/or Lewis acid sites. In zeolites, a Brønsted acidic proton can be a hydrogen atom bonded to the oxygen atom that connects the tetrahedrally coordinated aluminum which forms the zeolite structural framework. The Lewis acid centers in zeolites can contain tri-coordinated aluminum sites, which are electron deficient sites exhibiting the ability to accept electrons during interactions with molecules. In some aspects, the zeolite suitable for use in the zeolitic support as disclosed herein can be treated to reduce its acidity, for example by titration with a basic salt containing $Na^+$ and/or $K^+$ cations (e.g., by impregnation, ion-exchange, etc.). As will be appreciated by one of skill in the art, and with the help of this disclosure, and without wishing to be limited by theory, acidic sites in a zeolite can promote isomerization of n-butane to i-butane. In some aspects, the zeolitic support can be characterized by low acidity and/or low aluminum content; e.g., the zeolitic support can be characterized by low Brønsted acidity. In some aspects, the zeolitic support can be characterized by substantially no acidity (i.e., zero acidity).

In some aspects, the zeolitic support can be characterized by a weight ratio of silica to alumina ($SiO_2/Al_2O_3$) of equal to or greater than about 100, alternatively equal to or greater than about 150, alternatively equal to or greater than about 200, alternatively equal to or greater than about 250, alternatively equal to or greater than about 275, alternatively equal to or greater than about 300, alternatively from about 100 to about 400, alternatively from about 200 to about 350, alternatively from about 250 to about 300, alternatively from about 275 to about 290, or alternatively about 280. In an aspect, the zeolitic support (e.g., ZSM-5) can be characterized by a weight ratio of silica to alumina ($SiO_2/Al_2O_3$) of 280. As will be appreciated by one of skill in the art, and with the help of this disclosure, and without wishing to be limited by theory, the acidity of a support decreases with increasing its weight ratio of silica to alumina ($SiO_2/Al_2O_3$).

In an aspect, the zeolitic support can comprise a zeolite, wherein the zeolite can be selected from the group consisting of ZSM-5, ZSM-11, Y, high-silica Y, USY, EU-1, EU-2, beta, L, ferrierite, CHA, SSZ-16, Nu-3, Sigma-1, Silicalite-1, and combinations thereof.

In an aspect, the zeolitic support can be present in the hydrogenolysis bimetallic supported catalyst in an amount of from about 90 wt. % to about 99.9 wt. %, alternatively from about 95 wt. % to about 99.85 wt. %, or alternatively from about 99 wt. % to about 99.8 wt. %, based on the total weight of the hydrogenolysis bimetallic supported catalyst.

In an aspect, a hydrogenolysis bimetallic supported catalyst as disclosed herein can comprise a first metal, a second metal, and a zeolitic support; wherein the first metal comprises Pt, wherein the second metal comprises Ir, and wherein the zeolitic support comprises ZSM-5.

The hydrogenolysis bimetallic supported catalyst as disclosed herein can be made by using any suitable methodology. In an aspect, a method of making a hydrogenolysis bimetallic supported catalyst can comprise a wet impregnation step of contacting a zeolitic support with an aqueous metal precursor solution to form a bimetallic impregnated zeolitic support, wherein the aqueous metal precursor solution comprises a first metal precursor and a second metal precursor, and wherein the aqueous metal precursor solution is characterized by a weight ratio of the first metal to the second metal of from about 0.1:1 to about 10:1, alternatively from about 0.5:1 to about 7:1, or alternatively from about 1:1 to about 4:1.

The zeolitic support can be contacted with an aqueous metal precursor solution under agitating, stirring, magnetic stirring, sonicating, and the like, or combinations thereof. The zeolitic support can be contacted with an aqueous metal precursor solution for any suitable time period, for example a time period of from about 10 minutes to about 72 hours, alternatively from about 15 minutes to about 48 hours, alternatively from about 20 minutes to about 24 hours, alternatively from about 30 minutes to about 12 hours, alternatively from about 1 hour to about 6 hours, or alternatively from about 2 hours to about 4 hours.

The first metal precursor and/or the second metal precursor can comprise any suitable compound that contains the first metal and/or the second metal, respectively. For example, the first metal precursor and/or the second metal precursor can comprise chlorometallic acids, chlorides, nitrates, amines, acetylacetonates, and the like, or combinations thereof. In an aspect, the first metal precursor and/or the second metal precursor can comprise a chlorometallic acid comprising the first metal and/or the second metal, respectively; a chloride comprising the first metal and/or the second metal, respectively; a nitrate comprising the first metal and/or the second metal, respectively; an amine comprising the first metal and/or the second metal, respectively; an acetylacetonate comprising the first metal and/or the second metal, respectively; and the like; or combinations thereof.

Nonlimiting examples of the first metal precursor and/or the second metal precursor suitable for use in the present disclosure include chloroplatinic acid, chloroiridic acid, platinum chloride, iridium chloride, platinum nitrate, iridium nitrate, trichloroiridium pentaamine, platinum acetylacetonate, iridium acetylacetonate, and the like, or combinations thereof.

In some aspects, a method of making a hydrogenolysis bimetallic supported catalyst can comprise co-impregnating the zeolitic support with the first metal precursor and the second metal precursor. In such aspects, the zeolitic support can be contacted with an aqueous metal precursor solution comprising both the first metal precursor and the second metal precursor. The zeolitic support can be co-impregnated with the first metal precursor and the second metal precursor under agitating, stirring, magnetic stirring, sonicating, and the like, or combinations thereof. In an aspect, the zeolitic support can be co-impregnated with the first metal precursor and the second metal precursor at any suitable temperature, for example at room temperature, alternatively at a temperature of from about 15° C. to about 80° C., alternatively from about 20° C. to about 70° C., or alternatively from about 25° C. to about 60° C. In an aspect, the zeolitic support can be co-impregnated with the first metal precursor and the second metal precursor for any suitable time period, for example a time period of from about 10 minutes to about 72 hours, alternatively from about 15 minutes to about 48 hours, alternatively from about 20 minutes to about 24 hours, alternatively from about 30 minutes to about 12 hours, alternatively from about 1 hour to about 6 hours, or alternatively from about 2 hours to about 4 hours.

In other aspects, a method of making a hydrogenolysis bimetallic supported catalyst can comprise contacting a zeolitic support with a first aqueous metal precursor solution to form a monometallic impregnated zeolitic support, wherein the first aqueous metal precursor solution comprises the first metal precursor. In such aspects, the first metal precursor can comprise Pt.

The zeolitic support can be contacted with the first aqueous metal precursor solution under agitating, stirring, magnetic stirring, sonicating, and the like, or combinations thereof; and for a time period of from about 10 minutes to about 72 hours, alternatively from about 15 minutes to about 48 hours, alternatively from about 20 minutes to about 24 hours, alternatively from about 30 minutes to about 12 hours, alternatively from about 1 hour to about 6 hours, or alternatively from about 2 hours to about 4 hours.

The monometallic impregnated zeolitic support can be contacted with a second aqueous metal precursor solution to form the bimetallic impregnated zeolitic support, wherein the second aqueous metal precursor solution comprises the second metal precursor. The second metal precursor can comprise Ir, Rh, or both Ir and Rh.

The monometallic impregnated zeolitic support can be contacted with the second aqueous metal precursor solution under agitating, stirring, magnetic stirring, sonicating, and the like, or combinations thereof; and for a time period of from about 10 minutes to about 72 hours, alternatively from about 15 minutes to about 48 hours, alternatively from about 20 minutes to about 24 hours, alternatively from about 30 minutes to about 12 hours, alternatively from about 1 hour to about 6 hours, or alternatively from about 2 hours to about 4 hours.

In an aspect, a method of making a hydrogenolysis bimetallic supported catalyst can comprise a step of drying the bimetallic impregnated zeolitic support at a temperature of from about 70° C. to about 180° C., alternatively from about 70° C. to about 150° C., alternatively from about 70° C. to about 125° C., alternatively from about 70° C. to about 110° C., alternatively from about 80° C. to about 100° C., or alternatively from about 85° C. to about 95° C., to form a dry bimetallic impregnated zeolitic support. The bimetallic impregnated zeolitic support can be dried for a time period of from about 1 minute to about 1 month, alternatively from about 2.5 minutes to about 2 weeks, alternatively from about 5 minutes to about 1 week, alternatively from about 10 minutes to about 72 hours, alternatively from about 15 minutes to about 48 hours, alternatively from about 20 minutes to about 24 hours, alternatively from about 25 minutes to about 12 hours, alternatively from about 30 minutes to about 8 hours, alternatively from about 45 minutes to about 4 hours, or alternatively from about 1 hour to about 3 hours.

In aspects where the zeolitic support is contacted a with a first aqueous metal precursor solution to form a monometallic impregnated zeolitic support, the monometallic impregnated zeolitic support can be dried to form a dried monometallic impregnated zeolitic support, prior to contacting the monometallic impregnated zeolitic support (e.g., dried monometallic impregnated zeolitic support) with the second aqueous metal precursor. The monometallic impregnated zeolitic support can be dried at a temperature of from about 70° C. to about 180° C., alternatively from about 70° C. to about 150° C., alternatively from about 70° C. to about 125° C., alternatively from about 70° C. to about 110° C., alternatively from about 80° C. to about 100° C., or alternatively from about 85° C. to about 95° C.; and for a time period of from about 1 minute to about 1 month, alternatively from about 2.5 minutes to about 2 weeks, alternatively from about 5 minutes to about 1 week, alternatively from about 10 minutes to about 72 hours, alternatively from about 15 minutes to about 48 hours, alternatively from about 20 minutes to about 24 hours, alternatively from about 25 minutes to about 12 hours, alternatively from about 30 minutes to about 8 hours, alternatively from about 45 minutes to about 4 hours, or alternatively from about 1 hour to about 3 hours.

In an aspect, a method of making a hydrogenolysis bimetallic supported catalyst can comprise a step of calcining the bimetallic impregnated zeolitic support and/or the dry bimetallic impregnated zeolitic support under an oxidizing atmosphere at a temperature of less than about 550° C., alternatively less than about 450° C., alternatively less than about 350° C., alternatively less than about 320° C., alternatively from about 200° C. to about 550° C., alternatively from about 225° C. to about 450° C., alternatively from about 250° C. to about 350° C., or alternatively from about 280° C. to about 320° C., to form a calcined bimetallic impregnated zeolitic support. The oxidizing atmosphere can be any suitable atmosphere comprising oxygen, such as air, oxygen, technical oxygen, etc. The bimetallic impregnated zeolitic support and/or the dry bimetallic impregnated zeolitic support can be calcined for a time period of from about 30 minutes to about 72 hours, alternatively from about 45 minutes to about 48 hours, alternatively from about 1 hour to about 24 hours, alternatively from about 2 hours to about 12 hours, or alternatively from about 3 hours to about 6 hours.

In aspects where the zeolitic support is contacted with a first aqueous metal precursor solution to form a monometallic impregnated zeolitic support, the monometallic impregnated zeolitic support and/or the dried monometallic impregnated zeolitic support can be calcined under an oxidizing atmosphere to form a calcined monometallic impregnated zeolitic support, prior to contacting the monometallic impregnated zeolitic support (e.g., dried monometallic impregnated zeolitic support, calcined monometallic impregnated zeolitic support) with the second aqueous metal precursor. The monometallic impregnated zeolitic support and/or the dried monometallic impregnated zeolitic support can be calcined at a temperature of less than about 550° C., alternatively less than about 450° C., alternatively less than about 350° C., alternatively less than about 320° C., alternatively from about 200° C. to about 550° C., alternatively from about 225° C. to about 450° C., alternatively from about 250° C. to about 350° C., or alternatively from about 280° C. to about 320° C.; and for a time period of from about 30 minutes to about 72 hours, alternatively from about 45 minutes to about 48 hours, alternatively from about 1 hour to about 24 hours, alternatively from about 2 hours to about 12 hours, or alternatively from about 3 hours to about 6 hours.

In an aspect, a method of making a hydrogenolysis bimetallic supported catalyst can comprise a step of reducing the first metal and the second metal to form the hydrogenolysis bimetallic supported catalyst. For purposes of the disclosure herein, the term "reduce," "reducing," "reduced," etc. when used with respect to a metal, refer to the process of altering the oxidation state (i.e., oxidation number) of the metal; specifically, decreasing the oxidation state of the metal. For example, if a metal has an oxidation state of +3, the metal can be reduced to have an oxidation state of +2, +1, or 0. Generally, metals are reduced by accepting electrons in a reduction reaction. Without wishing to be limited by theory, reducing the first metal and the second metal provides for placing the first metal and the second metal in their catalytically active state with respect to hydrogenolysis. Further, and without wishing to be limited by theory, metals in their metallic form (i.e., oxidation state of 0) can be catalytically active with respect to hydrogenolysis; although metals having an oxidation state other than 0 can also be catalytically active with respect to hydrogenolysis.

In some aspects, reducing the first metal and/or the second metal can comprise contacting the first metal precursor and/or the second metal precursor, respectively, with a reducing medium. In such aspects, the first metal and/or the second metal can be reduced by contacting an aqueous metal precursor solution comprising the first metal and/or the second metal with a reducing medium. In such aspects, the wet impregnation step of contacting a zeolitic support with an aqueous metal precursor solution and the step of reducing the first metal and/or the second metal can occur about concurrently. The reducing medium can be added to the aqueous metal precursor solution. For example, the reducing medium can be sodium borohydride ($NaBH_4$).

In other aspects, reducing the first metal and the second metal can comprise contacting the calcined bimetallic impregnated zeolitic support with a reducing medium. In such aspects, the reducing medium can comprise hydrogen and/or carbon monoxide.

In an aspect, the reducing medium can comprise hydrogen, wherein the calcined bimetallic impregnated zeolitic support is contacted with hydrogen at a temperature of from about 300° C. to about 500° C., alternatively from about 350° C. to about 450° C., or alternatively from about 375° C. to about 425° C.; and for a time period of from about 1 minute to about 1 month, alternatively from about 2.5 minutes to about 2 weeks, alternatively from about 5 minutes to about 1 week, alternatively from about 10 minutes to about 72 hours, alternatively from about 15 minutes to about 48 hours, alternatively from about 20 minutes to about 24 hours, alternatively from about 25 minutes to about 12 hours, alternatively from about 30 minutes to about 8 hours, alternatively from about 45 minutes to about 4 hours, or alternatively from about 1 hour to about 3 hours In an aspect, the reducing medium can further comprise a hydrocarbon, such as butane (e.g., n-butane, i-butane). For example, the calcined bimetallic impregnated zeolitic support can be introduced to a reactor or reaction zone, wherein a reducing medium can be introduced to the reactor to reduce the first metal and the second metal, and wherein the reducing medium can comprise hydrogen and a hydrocarbon. In such aspects, the first metal and the second metal can be reduced about concurrently with the bimetallic impregnated zeolitic support catalyzing a hydrogenolysis reaction.

In an aspect, a process for selective hydrogenolysis can comprise introducing a butane feed stream and hydrogen to a hydrogenolysis reactor to produce a hydrogenolysis product stream, wherein the hydrogenolysis reactor comprises the hydrogenolysis bimetallic supported catalyst as disclosed herein, and wherein the hydrogenolysis product stream comprises hydrogen, methane, ethane, propane, i-butane, and optionally n-butane. In some aspects, the hydrogenolysis product stream can further comprise some impurities, such as $C_{5+}$ hydrocarbons. Generally, hydrogenolysis refers to a chemical reaction whereby a carbon-carbon or carbon-heteroatom single bond is cleaved or undergoes "lysis" by hydrogen, usually at relatively low temperatures (e.g., less than about 330° C.). For purposes of the disclosure herein, the term "selective hydrogenolysis" refers to a hydrogenolysis process wherein two or more different hydrocarbons (e.g., first hydrocarbon, second hydrocarbon; n-butane, i-butane) are subjected to a hydrogenolysis reaction, and wherein at least one hydrocarbon (e.g., first hydrocarbon; n-butane) undergoes hydrogenolysis, and wherein at least one hydrocarbon (e.g., second hydrocarbon; i-butane) is resistant to hydrogenolysis (e.g., has a low conversion in a hydrogenolysis reaction, such as less than about 20% conversion), under the same given set of reaction conditions (e.g., catalyst, pressure, temperature, flow rate, etc.). Generally, a conversion of a reagent or reactant refers to the percentage (usually mol %) of reagent that reacted to both undesired and desired products, based on the total amount (e.g., moles) of reagent present before any reaction took place. For purposes of the disclosure herein, the conversion of a reagent is a % conversion based on moles converted. Without wishing to be limited by theory, the hydrogenolysis reaction rate of the first hydrocarbon (e.g., n-butane) is greater than the hydrogenolysis reaction rate of the second hydrocarbon (e.g., i-butane), thereby allowing the separation (e.g., reactive separation) of n-butane and i-butane by consuming the n-butane in the hydrogenolysis reaction and recovering the unreacted i-butane. As will be appreciated by one of skill in the art, and with the help of this disclosure, the selective hydrogenolysis of n-butane from a butane feed stream comprising n-butane and i-butane provides for the reactive separation of n-butane from i-butane.

In an aspect, the butane feed stream can comprise n-butane and i-butane. In some aspects, the butane feed stream can comprise n-butane in an amount of equal to or greater than about 5 mol %, alternatively equal to or greater than about 10 mol %, alternatively equal to or greater than about 20 mol %, alternatively equal to or greater than about 30 mol %, alternatively equal to or greater than about 40 mol %, alternatively equal to or greater than about 50 mol %, alternatively equal to or greater than about 60 mol %, alternatively equal to or greater than about 70 mol %, alternatively equal to or greater than about 80 mol %, or alternatively equal to or greater than about 90 mol %.

The butane feed stream can comprise i-butane in an amount of equal to or greater than about 5 mol %, alternatively equal to or greater than about 10 mol %, alternatively equal to or greater than about 20 mol %, alternatively equal to or greater than about 30 mol %, alternatively equal to or greater than about 40 mol %, alternatively equal to or greater than about 50 mol %, alternatively equal to or greater than about 60 mol %, alternatively equal to or greater than about 70 mol %, alternatively equal to or greater than about 80 mol %, or alternatively equal to or greater than about 90 mol %.

In an aspect, the butane feed stream can be characterized by a mole ratio of n-butane to i-butane of equal to or greater than about 0.05:1, alternatively equal to or greater than about 0.1:1, alternatively equal to or greater than about 0.25:1, alternatively equal to or greater than about 0.5:1, alternatively equal to or greater than about 1:1, alternatively equal to or greater than about 2:1, alternatively equal to or greater than about 2.5:1, alternatively equal to or greater than about 5:1, alternatively equal to or greater than about 7.5:1, alternatively equal to or greater than about 10:1, alternatively from about 0.05:1 to about 10:1, alternatively from about 0.1:1 to about 7.5:1, alternatively from about 0.25:1 to about 5:1, or alternatively from about 0.5:1 to about 2.5:1

In an aspect, the butane feed stream can comprise n-butane in an amount of equal to or greater than about 50 mol %. In such aspect, the butane feed stream can comprise i-butane in an amount of less than about 50 mol %.

In an aspect, the butane feed stream can comprise field grade-butane (e.g., mixed butane). Field grade-butane is generally produced by natural gas processing and/or oil refining. Field-grade butane can comprise from about 50 mol % to about 80 mol %, alternatively from about 55 mol % to about 80 mol %, or alternatively from about 60 mol % to about 75 mol % n-butane; and from about 20 mol % to about 50 mol %, alternatively from about 20 mol % to about 45 mol %, or alternatively from about 25 mol % to about 40 mol % i-butane. Field-grade butane can further comprise from about 0 mol % to about 5 mol % propane and/or pentanes.

While the current disclosure will be discussed in detail in the context of a butane feed stream being introduced to a hydrogenolysis reactor comprising the hydrogenolysis bimetallic supported catalyst as disclosed herein for the reactive separation of i-butane from n-butane, it should be understood that any suitable type of hydrocarbon feed stream can be introduced to a hydrogenolysis reactor comprising the hydrogenolysis bimetallic supported catalyst as disclosed herein for the reactive separation of its components; for example a naphtha feed stream.

In an aspect, the hydrogenolysis reactor can comprise a fixed bed reactor, a radial flow reactor, a multi-layered bed reactor, a continuous flow reactor, an adiabatic reactor, an isothermal reactor, and the like, or combinations thereof.

The hydrogenolysis reactor can be characterized by a temperature of from about 200° C. to about 600° C., alternatively from about 250° C. to about 550° C., or alternatively from about 300° C. to about 500° C.

In some aspects, the hydrogenolysis reactor can be characterized by a temperature (e.g., hydrogenolysis temperature) of from about 200° C. to about 330° C., alternatively from about 250° C. to about 325° C., or alternatively from about 280° C. to about 310° C. As will be appreciated by one of skill in the art, and with the help of this disclosure, temperatures below 330° C. are conducive to selective hydrogenolysis. Generally, hydrocracking refers to a process that rearranges and breaks hydrocarbon chains, as well as adds hydrogen to unsaturated hydrocarbons to produce saturated hydrocarbons, at relatively high temperatures (e.g., greater than about 330° C.).

In other aspects, the reactor (e.g., hydrogenolysis reactor) can be characterized by a temperature (e.g., hydrocracking temperature) of from about 330° C. to about 600° C., alternatively from about 400° C. to about 550° C., or alternatively from about 425° C. to about 500° C. As will be appreciated by one of skill in the art, and with the help of this disclosure, temperatures above 330° C. are conducive to hydrocracking (as opposed to hydrogenolysis).

As will be appreciated by one of skill in the art, and with the help of this disclosure, and without wishing to be limited by theory, given the same feed stream, hydrogenolysis and hydrocracking will produce a different product distribution, owing to different reaction mechanisms, which can activate or inhibit different components of a given catalyst. For example, relatively high temperatures (e.g., hydrocracking temperatures, such as greater than about 400° C.) can inactivate one of the metals of the hydrogenolysis bimetallic supported catalyst as disclosed herein (e.g., can inactivate the second metal of the hydrogenolysis bimetallic supported catalyst as disclosed herein, for example Ir), thereby promoting cracking and hydrogenation of all components of the feed stream (e.g., n-butane and i-butane) in the presence of the first metal (e.g., Pt) that remains active on the support at such elevated temperatures. Further, as will be appreciated by one of skill in the art, and with the help of this disclosure, and without wishing to be limited by theory, relatively high temperatures (e.g., hydrocracking temperatures, such as greater than about 400° C.) are generally needed to get over the activation energy to begin cracking. Furthermore, as will be appreciated by one of skill in the art, and with the help of this disclosure, and without wishing to be limited by theory, the branched i-butane is a more stable molecule than the linear n-butane, and as such higher temperatures (e.g., greater than about 400° C.) are generally necessary to activate i-butane in a cracking process.

In an aspect, hydrogenolysis of the butane feed stream at relatively low temperatures (e.g., less than about 330° C.) can increase the amount of ethane in the hydrogenolysis product stream, as compared to the amount of ethane in a product stream obtained from an otherwise similar process that would be run at relatively high temperatures (e.g., greater than about 330° C.).

In an aspect, hydrocracking of the butane feed stream at relatively high temperatures (e.g., greater than about 330° C.) can increase the amount of propane and/or methane in the product stream, as compared to the amount of propane and/or methane, respectively in a product stream obtained from an otherwise similar process (e.g., hydrogenolysis process) that is run at relatively low temperatures (e.g., less than about 330° C.). Further, as will be appreciated by one of skill in the art, and with the help of this disclosure, and without wishing to be limited by theory, since hydrocracking converts i-butane as well, higher amounts of propane are expected than when converting only the linear n-butane (and not the branched i-butane).

In an aspect, a process can comprise introducing a butane feed stream and hydrogen to an adiabatic reactor to produce a product stream, wherein the adiabatic reactor comprises the hydrogenolysis bimetallic supported catalyst as disclosed herein, and wherein the product stream comprises hydrogen, methane, ethane, propane, i-butane, and optionally n-butane. An inlet temperature of the adiabatic reactor can be greater than about 200° C., wherein the butane feed stream can undergo selective hydrogenolysis in a first portion of the adiabatic reactor. Without wishing to be limited by theory, the temperature generally increases gradually along a length of the adiabatic reactor, from the inlet to the outlet, since the hydrogenolysis and hydrocracking are exothermic processes. As the gaseous mixture travels through (e.g., moves through) the reactor from the inlet to the outlet, the gaseous mixture undergoes hydrogenolysis up until the temperature reaches about 330° C., and subsequent to that, the gaseous mixture travelling through a second portion of the adiabatic reactor undergoes hydrocracking, at temperatures above 330° C.; wherein the second portion of the reactor is downflow of the first portion of the reactor. In such aspect, the process can advantageously utilize the heat of hydrogenolysis to promote the hydrocracking.

The hydrogenolysis reactor can be characterized by a pressure (e.g., hydrogenolysis pressure) of from about 0 psig to about 300 psig, alternatively from about 10 psig to about 300 psig, alternatively from about 20 psig to about 200 psig, alternatively from about 50 psig to about 150 psig, alternatively from about 75 psig to about 125 psig, or alternatively from about 90 psig to about 110 psig.

The hydrogenolysis reactor can be characterized by a hydrocarbon-based weight hourly space velocity (WHSV) of from about 0.1 $h^{-1}$ to about 15 $h^{-1}$, alternatively from about 0.5 $h^{-1}$ to about 10 $h^{-1}$, or alternatively from about 1 $h^{-1}$ to about 5 $h^{-1}$. Generally, the WHSV refers to a mass of reagents (e.g., hydrocarbons) fed per hour divided by a mass of catalyst used in a particular reactor.

The hydrogenolysis reactor can be characterized by a hydrogen to $C_4$ hydrocarbons molar ratio of from about 0.1:1 to about 10:1, alternatively from about 0.5:1 to about 7.5:1, or alternatively from about 1:1 to about 5:1.

In some aspects, the hydrogenolysis reactor can be operated under an optimal set of operational parameters that result in substantially consuming all of the n-butane in the hydrogenolysis reactor, wherein the hydrogenolysis product stream is substantially free of n-butane. For example, in order to substantially consume all of the n-butane in the hydrogenolysis reactor, the hydrogenolysis reactor can be operated at a WHSV of from about 3 $h^{-1}$ to about 5 $h^{-1}$, a pressure of from about 50 psig to about 100 psig, a hydrogen to $C_4$ hydrocarbons molar ratio of from about 2:1 to about 2.5:1, at a temperature of from about 280° C. to about 300° C.; and in the presence of a hydrogenolysis bimetallic supported catalyst comprising Pt and Ir supported on ZSM-5, wherein Pt is present in a total amount of from about 0.2 wt. % to about 0.4 wt. %, or alternatively about 0.3 wt. %, based on the total weight of the hydrogenolysis bimetallic supported catalyst; wherein Ir is present in a total amount of from about 0.2 wt. % to about 0.4 wt. %, or alternatively about 0.3 wt. %, based on the total weight of the hydrogenolysis bimetallic supported catalyst; wherein Pt and Ir are present in a weight ratio of Pt to Ir of from about 0.8:1 to about 1.2:1, or alternatively about 1:1; and wherein the ZSM-5 is characterized by a weight ratio of silica to alumina ($SiO_2/Al_2O_3$) of from about 250 to about 300, or alternatively about 280.

A process for selective hydrogenolysis as disclosed herein can comprise separating the hydrogenolysis product stream in a separation unit into its components.

In an aspect, at least a portion of the unreacted hydrogen can be separated from the hydrogenolysis product stream to yield recovered hydrogen. Hydrogen can be separated from the hydrogenolysis product stream by using any suitable separation technique, such as for example by pressure swing adsorption (PSA), membrane separation, cryogenic separation, etc. At least a portion of the recovered hydrogen can be recycled to the hydrogenolysis reactor.

In an aspect, at least a portion of the methane can be separated from the hydrogenolysis product stream to yield a methane stream. Methane can be separated from the hydrogenolysis product stream by using any suitable separation technique, such as for example by distillation, e.g., in a demethanizer. The methane stream can be used in any suitable process or application, such as fuel combustion, methane pyrolysis, methanation, hydrogen production, etc.

In an aspect, at least a portion of the ethane and/or propane can be separated from the hydrogenolysis product stream to yield an ethane and/or propane stream. Ethane and/or propane can be separated from the hydrogenolysis product stream by using any suitable separation technique, such as for example by distillation, e.g., in a deethanizer and/or depropanizer respectively. The ethane and/or propane stream can be fed to a gas steam cracker furnace to produce ethylene, and optionally propylene.

In an aspect, at least a portion of the unreacted i-butane can be separated from the hydrogenolysis product stream to yield an i-butane stream. i-butane can be separated from the hydrogenolysis product stream by using any suitable separation technique, such as for example by distillation. In aspects where the hydrogenolysis product stream comprises unreacted i-butane and unreacted n-butane, i-butane can be separated from n-butane by cryogenic distillation. The recovered unreacted n-butane can be recycled to the hydrogenolysis reactor. The i-butane stream can be used in any suitable process, for example the i-butane stream can be further hydrocracked to produce ethane; the i-butane stream can be further dehydrogenated to produce isobutylene; etc.

In an aspect, the hydrogenolysis reactor can be characterized by an i-butane conversion that is less than an n-butane conversion. As will be appreciated by one of skill in the art, and with the help of this disclosure, the conversion of reagents in hydrogenolysis is dependent on a variety of reactor conditions, such as flow rate, temperature, etc.

In an aspect, the hydrogenolysis reactor can be characterized by an i-butane conversion of less than about 25%, alternatively less than about 20%, alternatively less than about 15%, alternatively less than about 10%, alternatively less than about 5%, alternatively less than about 1%, alternatively less than about 0.5%, alternatively less than about 0.1%, alternatively less than about 0.01%, or alternatively less than about 0.001%.

In an aspect, the hydrogenolysis reactor can be characterized by a n-butane conversion of equal to or greater than about 75%, alternatively equal to or greater than about 80%, alternatively equal to or greater than about 85%, alternatively equal to or greater than about 90%, alternatively equal to or greater than about 95%, or alternatively equal to or greater than about 99%.

In some aspects, the hydrogenolysis reactor can be characterized by an i-butane conversion of less than about 25%, and by a n-butane conversion of equal to or greater than about 90%.

In an aspect, the hydrogenolysis bimetallic supported catalyst as disclosed herein can be characterized by a selectivity to ethane of from about 60 mol % to about 90 mol %, alternatively from about 65 mol % to about 85 mol %, or alternatively from about 70 mol % to about 80 mol %. Generally, a selectivity to a desired product or products refers to how much desired carbon product was formed divided by the total carbon products formed, both desired and undesired. For purposes of the disclosure herein, the selectivity to a desired product is a % selectivity based on moles converted into the desired product.

In an aspect, the hydrogenolysis bimetallic supported catalyst as disclosed herein can be characterized by a selectivity to methane of less than about 20 mol %, alternatively less than about 15 mol %, or alternatively less than about 12.5 mol %.

In an aspect, the hydrogenolysis bimetallic supported catalyst as disclosed herein can be characterized by a selectivity to propane of less than about 15 mol %, alternatively less than about 12.5 mol %, or alternatively less than about 10 mol %.

In an aspect, the hydrogenolysis bimetallic supported catalyst as disclosed herein, and methods of making and using same, can advantageously display improvements in one or more catalyst characteristics when compared to conventional hydrogenolysis catalysts, e.g., hydrogenolysis catalysts comprising a single metal and/or a non-zeolitic support.

In an aspect, the hydrogenolysis bimetallic supported catalyst as disclosed herein can advantageously display an increased selectivity to ethane, when compared to conventional hydrogenolysis catalysts. In an aspect, the hydrogenolysis bimetallic supported catalyst as disclosed herein can advantageously display a decreased selectivity to propane, when compared to conventional hydrogenolysis catalysts. Ethane can be converted more efficiently to ethylene, as compared to propane, for example, and as such the hydrogenolysis bimetallic supported catalyst as disclosed herein can advantageously render the production of ethylene from a butane stream more cost effective.

In an aspect, the hydrogenolysis bimetallic supported catalyst as disclosed herein can advantageously display a decreased selectivity to methane, when compared to conventional hydrogenolysis catalysts. By producing less methane, the hydrogenolysis bimetallic supported catalyst can advantageously enable the production of an increased amount of ethane, which can be further converted to ethylene.

In an aspect, the hydrogenolysis bimetallic supported catalyst as disclosed herein can advantageously provide for a relatively clean product slate of selective butane hydrogenolysis (e.g., methane, ethane, propane), which can in turn provide for a simplified downstream separation process.

In an aspect, the hydrogenolysis bimetallic supported catalyst as disclosed herein can advantageously provide for reactive separation of n-butane and i-butane. The hydrogenolysis bimetallic supported catalyst as disclosed herein can advantageously provide for lowering the hydrogenolysis temperature, thus making sintering less likely.

In an aspect, the hydrogenolysis bimetallic supported catalyst as disclosed herein can advantageously provide for improved (e.g., better) dispersion of catalytically active metals throughout the catalyst, thereby leading to a catalyst with increased stability, and thus longer life time. Additional advantages of the hydrogenolysis bimetallic supported catalyst as disclosed herein, and methods of making and using same, can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

The hydrogenolysis bimetallic supported catalyst as disclosed herein was prepared by wet sequential impregnation as follows. A monometallic supported catalyst was prepared by impregnating the first metal on zeolite support via contacting a zeolite support with a first metal precursor solution via wet impregnation, followed by drying at 90° C. and then by calcining at a temperature of 280° C. The second metal was impregnated on the monometallic zeolite supported catalyst by contacting a second metal precursor solution with the monometallic zeolite supported catalyst, followed by drying at 90° C. and then by calcining at a temperature of 280° C. A more detailed procedure is as follows.

Catalyst A ($Ir/Al_2O_3$)—conventional catalyst: A monometallic supported catalyst was prepared by wet co-impregnation: (1) A solution containing 1.0 wt. % of iridium (III) chloride was made by dissolving 0.019 g of iridium (III) chloride in 4.0 g of D.I. water in a 50 ml glass beaker. The salt (iridium (III) chloride) was not readily soluble in water at room temperature and had to be heated slightly (around 60° C.) to dissolve it. The solution was stirred continuously. (2) The gamma-alumina powder (5.0 g) was added to the Ir salt solution and stirred for 3 hours covered with glass lid, after which it was placed in a drying oven. The solution with alumina was evaporated at 90° C. and was dried for 2 hours. (3) The dried powder was calcined at 280° C. using the following calcination profile. The calcination profile was: room temperature (RT) to 100° C. (ramp 2° C./min), held for 8 h; followed by 100° C. to 280° C. (ramp 2° C./min), held for 3 h. Catalyst A ($Ir/Al_2O_3$) contained 1 wt. % Ir supported on alumina (from Sasol).

Catalyst B (Ir—$Pt/Al_2O_3$)—conventional catalyst: A bimetallic supported catalyst (Ir-0.15 wt. %, Pt-0.15 wt. %) was prepared by wet co-impregnation. (1) An aqueous solution was made by dissolving 0.019 g of the iridium trichloride hydrate ($IrCl_3 \cdot xH_2O$) in 3.0 g of water in a 50 ml glass beaker. The salt ($IrCl_3 \cdot xH_2O$) was not readily soluble in water at room temperature and was heated slightly (around 60° C.) to dissolve it. The solution was stirred continuously. (2) Similarly, an aqueous solution was made by dissolving 0.023 g of chloroplatinic acid hexahydrate in 1.0 g of D.I water in a 25 ml glass beaker. (3) The two solutions were mixed together. (4) The gamma-alumina powder (from Sasol corporation) (5.0 g) was added to this solution and stirred for 3 hours covered. The powder was dried at 90° C. for 2 hours. (3) The dried powder was calcined at 280° C. using the same calcination profile as for Catalyst A. Catalyst B (Ir—$Pt/Al_2O_3$) contained 0.15 wt. % Ir and 0.15 wt. % Pt supported on alumina (from Sasol).

Catalyst C (Ir/ZSM-5): 0.026 g of $IrCl_3$ was dissolved in water by heating the solution. Then, 5.0 g of ZSM-5 extrudates (obtained from Zeolyst Inc.) made by using ZSM-5 powder having $SiO_2/Al_2O_3$ ratio of 280 with 20 wt. % alumina as binder, were added to the Ir salt solution and synthesis was carried as described for Catalyst A. Catalyst C (Ir/ZSM-5) contained 0.3 wt. % Ir supported on ZSM-5, wherein the ZSM-5 support was characterized by a weight ratio of silica to alumina ($SiO_2/Al_2O_3$) of 50.

Catalyst D (Ir,Pt/ZSM-5): 0.031 g of $IrCl_3$ was dissolved in water by heating the solution. Then, a solution containing 0.046 g of chloroplatinic acid was added to the Ir salt solution. Then, 5.0 g of ZSM-5 extrudates (obtained from Zeolyst Inc.) made by using ZSM-5 powder having $SiO_2/Al_2O_3$ ratio of 280 with 20 wt. % alumina as binder, were added to the Ir salt solution and synthesis was carried as described for Catalyst B. Catalyst D (Ir,Pt/ZSM-5) contained 0.3 wt. % Ir and 0.3 wt. % Pt supported on ZSM-5, wherein the ZSM-5 support was characterized by a weight ratio of silica to alumina ($SiO_2/Al_2O_3$) of 280.

Example 2

The following table (Table 1) shows the catalytic activity and selectivity comparison of different catalysts. As shown below, the Ir/Pt bimetallic catalyst supported on ZSM-5 results in the highest selectivity for ethane, 76 mol %, compared to conventional catalysts, such as $Ir/Al_2O_3$. In addition, by forming the Ir,Pt bimetallic catalyst, $C_2$ selectivity can be increased from 8% in Ir/ZSM-5 to 76% in Ir,Pt/ZSM-5.

TABLE 1

Activity and Selectivity of Selective Hydrogenolysis at Different Reaction Conditions (WHSV = 4 $h^{-1}$, $H_2$/HC = 2.5, 100 psig)

| Catalyst | Feed | Temp (° C.) | n-Butane Conversion (%) | Iso-Butane Conversion (%) | Ethane (mol %) | Methane (mol %) | Propane (mol %) | Other $C_4$ (mol %) |
|---|---|---|---|---|---|---|---|---|
| Catalyst A | n-butane | 275 | 20 | — | 62 | 20 | 18 | 0 |
| Catalyst B | 70% n-butane/ 30% i-butane | 300 | 3 | — | 8 | 22 | 24 | 46 |
| Catalyst C | 70% n-butane/ 30% i-butane | 300 | 62 | 4 | 70 | 17 | 13 | 0 |
| Catalyst D | 70% n-butane/ 30% i-butane | 300 | 98 | 11 | 76 | 15 | 9 | 0.02 |

By comparing the performance of the two conventional catalysts in Table 1, the addition of Pt to the $Ir/Al_2O_3$ catalyst (resulting in Catalyst B) leads to an increase in methane selectivity, an increase in propane selectivity, an increase in $C_4$ selectivity, as well as a decreased ethane selectivity. As such, it would be expected that adding Pt to the Ir/ZSM-5 catalyst would provide for a similar trend in the resulting selectivity. However, the data in Table 1 shows the surprising and unexpected result that the addition of Pt to the Ir/ZSM-5 catalyst (resulting in Catalyst D) provides for a decrease in methane selectivity, a decrease in propane selectivity, as well as an increase in ethane selectivity.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

Additional Disclosure

A first aspect, which is a hydrogenolysis bimetallic supported catalyst comprising a first metal, a second metal, and a zeolitic support; wherein the first metal and the second metal are different; and wherein the first metal and the second metal can each independently be selected from the group consisting of iridium (Ir), platinum (Pt), rhodium (Rh), ruthenium (Ru), palladium (Pd), molybdenum (Mo), tungsten (W), nickel (Ni), and cobalt (Co).

A second aspect, which is the hydrogenolysis bimetallic supported catalyst of the first aspect; wherein the zeolitic support comprises a zeolite; wherein the zeolite is selected from the group consisting of ZSM-5, ZSM-11, Y, high-silica Y, USY, EU-1, EU-2, beta, L, ferrierite, CHA, SSZ-16, Nu-3, Sigma-1, Silicalite-1, and combinations thereof; wherein the zeolitic support further comprises a binder; and wherein the binder comprises alumina, titania, silica, or combinations thereof.

A third aspect, which is the hydrogenolysis bimetallic supported catalyst of the first and the second aspects, wherein the first metal and the second metal are present in a total amount of from about 0.2 wt. % to about 1 wt. %, based on the total weight of the hydrogenolysis bimetallic supported catalyst.

A fourth aspect, which is the hydrogenolysis bimetallic supported catalyst of any of the first through the third aspects, wherein the first metal and the second metal are present in a weight ratio of first metal to second metal of from about 0.3:1 to about 3:1.

A fifth aspect, which is the hydrogenolysis bimetallic supported catalyst of any of the first through the fourth aspects, wherein the zeolitic support is characterized by a weight ratio of silica to alumina ($SiO_2/Al_2O_3$) of equal to or greater than about 100.

A sixth aspect, which is the hydrogenolysis bimetallic supported catalyst of any of the first through the fifth aspects, wherein the first metal comprises Pt, wherein Pt is present in a total amount of from about 0.2 wt. % to about 0.4 wt. %, preferably about 0.3 wt. %, based on the total weight of the hydrogenolysis bimetallic supported catalyst; wherein the second metal comprises Ir, wherein Ir is present in a total amount of from about 0.2 wt. % to about 0.4 wt. %, preferably about 0.3 wt. %, based on the total weight of the hydrogenolysis bimetallic supported catalyst; wherein Pt and Ir are present in a weight ratio of Pt to Ir of from about 0.8:1 to about 1.2:1, preferably about 1:1; wherein the zeolitic support comprises ZSM-5; and wherein the zeolitic support is characterized by a weight ratio of silica to alumina ($SiO_2/Al_2O_3$) of from about 250 to about 300, preferably about 280.

A seventh aspect, which is a method of making a hydrogenolysis bimetallic supported catalyst comprising: (a) contacting a zeolitic support with an aqueous metal precursor solution to form a bimetallic impregnated zeolitic support, wherein the aqueous metal precursor solution comprises a first metal precursor and a second metal precursor, and wherein the aqueous metal precursor solution is characterized by a weight ratio of the first metal to the second metal of from about 0.1:1 to about 10:1; (b) drying the bimetallic impregnated zeolitic support at a temperature of from about 70° C. to about 180° C. to form a dry bimetallic impregnated zeolitic support; (c) calcining the dry bimetallic impregnated zeolitic support under an oxidizing atmosphere at a temperature of from about 200° C. to about 550° C. to form a calcined bimetallic impregnated zeolitic support; and (d) reducing the first metal and the second metal to form the hydrogenolysis bimetallic supported catalyst of any of the first though the sixth aspects.

An eighth aspect, which is the method of the seventh aspect, wherein the step (d) of reducing the first metal and the second metal comprises contacting the calcined bimetallic impregnated zeolitic support with a reducing medium at a temperature of from about 300° C. to about 500° C.

A ninth aspect, which is the method of the eighth aspect, wherein the reducing medium comprises hydrogen, and optionally a hydrocarbon and/or carbon monoxide.

A tenth aspect, which is the method of ninth aspect, wherein the calcined bimetallic impregnated zeolitic support is contacted with hydrogen at a temperature of from about 300° C. to about 500° C.

An eleventh aspect, which is the method of the seventh aspect, wherein the step (d) of reducing the first metal and the second metal comprises contacting the first metal precursor and/or a second metal precursor with a reducing medium.

A twelfth aspect, which is the method of the eleventh aspect, wherein steps (a) and (d) occur about concurrently.

A thirteenth aspect, which is the method of any of the seventh through the twelfth aspects, wherein step (a) comprises co-impregnating the zeolitic support with the first metal precursor and the second metal precursor.

A fourteenth aspect, which is the method of any of the seventh through the twelfth aspects, wherein step (a) comprises (i) contacting a zeolitic support with a first aqueous metal precursor solution to form a monometallic impregnated zeolitic support, wherein the first aqueous metal precursor solution comprises the first metal precursor; and (ii) contacting the monometallic impregnated zeolitic support with a second aqueous metal precursor solution to form the bimetallic impregnated zeolitic support, wherein the second aqueous metal precursor solution comprises the second metal precursor.

A fifteenth aspect, which is the method of any of the seventh through the fourteenth aspects, wherein the first metal comprises Pt, and wherein the second metal comprises Ir.

A sixteenth aspect, which is the method of any of the seventh through the fifteenth aspects, wherein the dry bimetallic impregnated zeolitic support is calcined for a time period of from about 30 minutes to about 72 hours.

A seventeenth aspect, which is a process for selective hydrogenolysis comprising introducing a butane feed stream and hydrogen to a hydrogenolysis reactor to produce a hydrogenolysis product stream, wherein the hydrogenolysis reactor comprises the hydrogenolysis bimetallic supported catalyst of any of the first through the sixth aspects, wherein the butane feed stream comprises n-butane and i-butane, wherein the hydrogenolysis product stream comprises hydrogen, methane, ethane, propane, i-butane, and optionally n-butane; and wherein the hydrogenolysis reactor is characterized by an i-butane conversion that is less than an n-butane conversion.

An eighteenth aspect, which is the process of the seventeenth aspect, wherein the hydrogenolysis reactor is characterized by a temperature of from about 200° C. to about 330° C.; a pressure of from about 0 psig to about 300 psig; a hydrocarbon-based weight hourly space velocity (WHSV) of from about 0.1 $h^{-1}$ to about 15 $h^{-1}$; and a hydrogen to $C_4$ hydrocarbons molar ratio of from about 0.1:1 to about 10:1.

A nineteenth aspect, which is the process of any of the seventeenth and the eighteenth aspects, wherein the hydrogenolysis reactor is characterized by an i-butane conversion of less than about 25%; and/or wherein the hydrogenolysis reactor is characterized by a n-butane conversion of equal to or greater than about 90%.

A twentieth aspect, which is the process of any of the seventeenth through the nineteenth aspects, wherein the hydrogenolysis bimetallic supported catalyst is characterized by (i) a selectivity to ethane of from about 60 mol % to about 90 mol %; (ii) a selectivity to methane of less than about 20 mol %; (iii) a selectivity to propane of less than about 15 mol %; or (iv) any combinations of (i)-(iii).

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A hydrogenolysis bimetallic supported catalyst comprising a first metal, a second metal, and a zeolitic support; wherein the first metal and the second metal are different; wherein the first metal and the second metal are present in a total amount of from about 4 wt. % to about 0.8 wt. %, based on the total weight of the hydrogenolysis bimetallic supported catalyst; wherein the first metal comprises platinum (Pt), wherein Pt is present in a total amount of from about 0.2 wt. % to about 0.4 wt. %, based on the total weight of the hydrogenolysis bimetallic supported catalyst, wherein the second metal comprises Ir, wherein Ir is present in a total amount of from about 0.2 wt. % to about 0.4 wt. % based on the total weight of the hydrogenolysis bimetallic supported catalyst; wherein Pt and Ir are present in a weight ratio of Pt to Ir of from about 0.8:1 to about 1.2:1; wherein the zeolite support comprises ZSM-5; and wherein the zeolitic support is characterized by a weight ratio of silica to alumina ($SiO_2/Al_2O_3$) of from about 250 to about 300.

2. The hydrogenolysis bimetallic supported catalyst of claim 1; wherein the zeolitic support comprises an additional zeolite and/or a binder; wherein the additional zeolite is selected from the group consisting of ZSM-11, Y, high-silica Y, USY, EU-1, EU-2, beta, L, ferrierite, CHA, SSZ-16, Nu-3, Sigma-1, Silicalite-1, and combinations thereof; and wherein the binder comprises alumina, titania, silica, or combinations thereof.

3. The hydrogenolysis bimetallic supported catalyst of claim 1, wherein the zeolitic support is characterized by a weight ratio of silica to alumina ($SiO_2/Al_2O_3$) of about 280.

4. A method of making a hydrogenolysis bimetallic supported catalyst comprising:
   (a) contacting a zeolitic support with an aqueous metal precursor solution to form a bimetallic impregnated zeolitic support, wherein the aqueous metal precursor solution comprises a first metal precursor and a second metal precursor, and wherein the aqueous metal precursor solution is characterized by a weight ratio of Pt to IR of from about 0.8:1 to about 1.2:1;
   (b) drying the bimetallic impregnated zeolitic support at a temperature of from about 70° C. to about 180° C. to form a dry bimetallic impregnated zeolitic support;
   (c) calcining the dry bimetallic impregnated zeolitic support under an oxidizing atmosphere at a temperature of from about 200° C. to about 550° C. to form a calcined bimetallic impregnated zeolitic support; and
   (d) reducing the Pt and the Ir to form the hydrogenolysis bimetallic supported catalyst of claim 1.

5. The method of claim 4, wherein the step (d) of reducing the Pt and the Ir comprises contacting the calcined bimetallic impregnated zeolitic support with a reducing medium at a temperature of from about 300° C. to about 500° C.

6. The method of claim 5, wherein the reducing medium comprises hydrogen, and optionally a hydrocarbon and/or carbon monoxide.

7. The method of claim 6, wherein the calcined bimetallic impregnated zeolitic support is contacted with hydrogen at a temperature of from about 300° C. to about 500° C.

8. The method of claim 4, wherein the step (d) of reducing the Pt and the Ir comprises contacting the first metal precursor and/or the second metal precursor with a reducing medium.

9. The method of claim 8, wherein steps (a) and (d) occur about concurrently.

10. The method of claim 4, wherein step (a) comprises co-impregnating the zeolitic support with the first metal precursor and the second metal precursor.

11. The method of claim 4, wherein step (a) comprises (i) contacting a zeolitic support with a first aqueous metal precursor solution to form a monometallic impregnated zeolitic support, wherein the first aqueous metal precursor solution comprises the first metal precursor; and (ii) contacting the monometallic impregnated zeolitic support with a second aqueous metal precursor solution to form the bimetallic impregnated zeolitic support, wherein the second aqueous metal precursor solution comprises the second metal precursor.

12. The method of claim 4, wherein the dry bimetallic impregnated zeolitic support is calcined for a time period of from about 30 minutes to about 72 hours.

13. A process for selective hydrogenolysis comprising introducing a butane feed stream and hydrogen to a hydrogenolysis reactor to produce a hydrogenolysis product stream, wherein the hydrogenolysis reactor comprises the hydrogenolysis bimetallic supported catalyst of claim 1, wherein the hydrogenolysis reactor is characterized by a temperature of from about 200° C. to about 330° C., wherein the butane feed stream comprises n-butane and i-butane, wherein the hydrogenolysis product stream comprises hydrogen, methane, ethane, propane, i-butane, and optionally n-butane; and wherein the hydrogenolysis reactor is characterized by an i-butane conversion that is less than an n-butane conversion.

14. The process of claim 13, wherein the hydrogenolysis reactor is characterized by a pressure of from about 0 psig to about 300 psig; a hydrocarbon-based weight hourly space velocity (WHSV) of from about 0.1 h$^{-1}$ to about 15 h$^{-1}$; and a hydrogen to $C_4$ hydrocarbons molar ratio of from about 0.1:1 to about 10:1.

15. The process of claim 13, wherein the hydrogenolysis reactor is characterized by an i-butane conversion of less than about 25%; and/or wherein the hydrogenolysis reactor is characterized by a n-butane conversion of equal to or greater than about 90%.

16. The process of claim 13, wherein the hydrogenolysis bimetallic supported catalyst is characterized by (i) a selectivity to ethane of from about 60 mol % to about 90 mol %; (ii) a selectivity to methane of less than about 20 mol %; (iii) a selectivity to propane of less than about 15 mol %; or (iv) any combinations of (i)-(iii).

17. The hydrogenolysis bimetallic supported catalyst of claim 1, wherein Pt is present in a total amount of about 0.3 wt. %, based on the total weight of the hydrogenolysis bimetallic supported catalyst; wherein Ir is present in a total amount of about 0.3 wt. %, based on the total weight of the hydrogenolysis bimetallic supported catalyst; and wherein the zeolitic support is characterized by a weight ratio of silica to alumina ($SiO_2/Al_2O_3$) of about 280.

18. The method of claim 7, wherein the calcined bimetallic impregnated zeolitic support is contacted with hydrogen at a temperature of from about 350° C. to about 450° C., and for a time period of from about 30 minutes to about 8 hours.

19. The process of claim 13, wherein the hydrogenolysis reactor is characterized by an i-butane conversion of less than about 15%, and wherein the hydrogenolysis reactor is characterized by a n-butane conversion of equal to or greater than about 95%.

20. The process of claim 1, wherein Pt and Ir are present in a weight ratio of Pt to Ir of about 1:1.

* * * * *